United States Patent [19]

Thomas

[11] Patent Number: 5,009,617

[45] Date of Patent: Apr. 23, 1991

[54] ASSEMBLY FOR A D.C. HID LAMP

[75] Inventor: Brian J. Thomas, Phoenix, N.Y.

[73] Assignee: Welch Allyn, Inc., Skaneateles Falls, N.Y.

[21] Appl. No.: 475,933

[22] Filed: Feb. 6, 1990

[51] Int. Cl.[5] .................................. H01R 13/64
[52] U.S. Cl. ................................ 439/679; 439/239
[58] Field of Search ............... 439/239, 240, 241, 242, 439/243, 235, 152, 678, 679, 488–491, 612, 617–619

[56] References Cited

U.S. PATENT DOCUMENTS

| | | | |
|---|---|---|---|
| 1,523,570 | 1/1925 | Winter et al. | 439/679 |
| 2,470,518 | 5/1949 | Orr | 439/618 |
| 2,957,158 | 10/1960 | Kennet | 439/617 |
| 3,233,207 | 2/1966 | Akroni et al. | 439/678 |
| 4,202,351 | 5/1980 | Biche | 439/491 |
| 4,386,818 | 6/1983 | Millhimes | 439/490 |
| 4,533,851 | 8/1985 | Block et al. | 439/617 |
| 4,820,193 | 4/1989 | Noorily | 439/491 |

FOREIGN PATENT DOCUMENTS 2170363 7/1986 United Kingdom ............... 439/678

*Primary Examiner*—David L. Pirlot
*Attorney, Agent, or Firm*—Wall and Roehrig

[57] ABSTRACT

A combination socket assembly and D.C. lamp apparatus. The lamp apparatus has first and second electric pin conductors protruding therefrom. The first pin conductor has a transverse configuration distinct from a transverse configuration of the second pin conductor. The socket assembly comprises a frame, a socket member, and a pair of metal contact clips. The socket element is mounted to the frame and receives the first and the second pin conductors of the lamp apparatus. The socket element contains first and second receptacles. The first receptacle is configured and dimensioned to mate with the first pin conductor and to prevent mating with the second pin conductor. The second receptacle is configured and dimensioned to mate with the second conductor. The metal contact clips are contained within the first and the second receptacles of the socket element. The metal contact clips are used to make electrical contact with the first and the second pin conductors of the lamp apparatus, whereby electrical current from an external power supply can be transmitted through the socket element to the lamp apparatus. The lamp apparatus includes a reflector assembly having a convex exterior surface. The convex exterior surface contains an indicia, covering a portion thereof for guiding a person in correctly orienting the lamp apparatus relative to the socket assembly.

4 Claims, 2 Drawing Sheets

ASSEMBLY FOR A D.C. HID LAMP

Background of the Invention

The present invention is directed to the general field of high intensity discharge (HID) lamps and, in particular, to socket assemblies for such lamps.

In a typical D.C. HID lamp an anode and a cathode are inserted into an arc chamber in spaced apart relation to each other. The anode and cathode each have an electrode tip. Together, the tips define a discharge path between which an arc travels when the lamp is in operation.

The anode and cathode are usually connected to respective foil seals which are, in turn, connected to respective inleads. The inleads provide the physical input to the lamp for electrical current during starting and operation of the lamp.

In many applications, including projection equipment or medical and dental instruments and illumination, a HID lamp is operated in conjunction with an optical system that comprises a concave reflector. The lamp is cemented into a collar of the reflector such that the lamp's position is substantially along the optical axis of the reflector. Each inlead of the lamp is connected to a respective pin conductor mounted in the collar of the reflector. The pin conductors project from the collar and provide a means for supplying electrical current to the lamp from an external D.C. power source.

In many practical implementations, the power source is connected to an electrical socket. The socket is configured to mate with the pin conductors, and thus complete an electrical circuit between the power source and the lamp.

In order for the lamp to function properly, the pin conductors must be mated with the socket in matching polarity. If the polarity is reversed, the lamp may not operate, or may operate inefficiently and have a considerably shortened lifespan.

A conventional socket assembly for a D.C. lamp contains positive and negative receptacles that are substantially uniform in configuration. There is nothing inherent in the design of the conventional socket assembly that will distinguish the positive receptacle from the negative receptacle. Moreover, the conventional design fails to ensure that the lamp will not be received by the socket in reverse polarity.

In many D.C. lamp applications directed to projector equipment or medical and dental instruments, the lifetime of the lamp is substantially shorter in comparison to the life-time of the instrument or equipment. Thus, the operator will be required to replace a failed lamp on several occasions over the life-time of the instrument or equipment. Normally, the operator will not be a skilled technician in electricity, and will be required to effectuate replacement of the lamp in an expeditious, manner. These circumstances present a significant risk that the D.C. lamp will be inserted into the socket in reverse polarity. Therefore, expedient replacement of a failed lamp is not realized for many applications.

OBJECTS AND SUMMARY OF THE INVENTION

It is, therefore, an object of this invention to provide an assembly that avoids the problems associated with the prior art.

Another object of the present invention is to provide an assembly configured to achieve expedient replacement of a D.C. lamp in its intended applications.

A further object of this invention is provide a socket assembly configured to ensure that the D.C. lamp is not inserted therein in reverse polarity.

Still another object of this invention is to provide a socket assembly and a lamp apparatus having indicia thereon for guiding the operator in correctly aligning the pin conductors of the lamp with the receptacles of the socket assembly.

Yet another object of this invention is to provide a method of ensuring that a D.C. lamp is not inserted into a socket assembly in reverse polarity.

These and other objects are attained in accordance with the present invention wherein there is provided a combination socket assembly and lamp apparatus. The lamp apparatus has first and second electric pin conductors protruding therefrom. The first pin conductor has a transverse configuration that is distinct from the transverse configuration of the second pin conductor. The socket assembly comprises a frame, and socket means mounted to the frame for receiving the first and the second pin conductors of the lamp apparatus. The socket means contains first and second receptacles. The first receptacle is configured and dimensioned to mate with the first pin conductor of the lamp apparatus and prevent such mating with the second pin conductor of the lamp apparatus. The second receptacle is configured and dimensioned to mate with the second pin conductor. The socket assembly further comprises conductive means, contained within the first and the second receptacles of the socket means, for making electrical contact with the first and the second pin conductors of the lamp apparatus. Therefore, electrical current from an external power supply can be transmitted through the socket means to the lamp apparatus.

BRIEF DESCRIPTION OF THE DRAWINGS

One way of carrying out the invention is described in detail below with reference to drawings which illustrate two specific embodiments, in which.

DETAILED DESCRIPTION OF THE INVENTION

Figure 1:
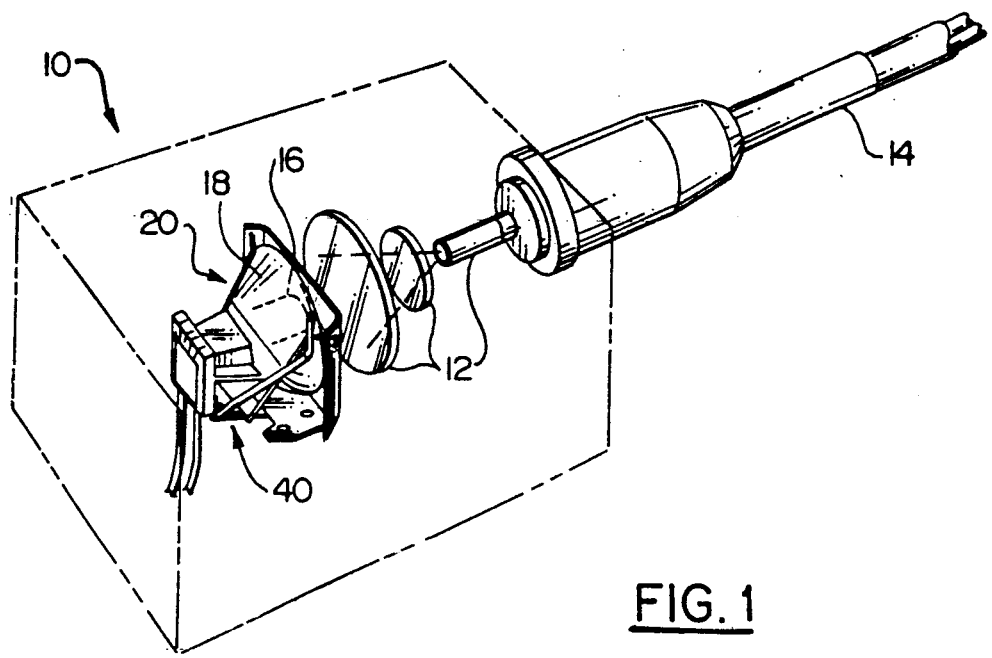
FIG. 1 is a reduced top and side perspective view of an instrument embodying the teachings of the present invention.

Referring now to FIG. 1 of the drawings, there is shown a perspective schematic view of a medical instrument 10 containing the preferred embodiment of the present invention. Instrument 10 could be, for example, an endoscope system or a dental curing apparatus for polymerizing dental restorative compositions. Instrument 10 includes an optical system 12 coupled to a light wave guide 14. The light source for instrument 10 is a direct current (D.C.) high intensity discharge lamp 16 mounted in a reflector assembly 18. The combination of lamp 16 and reflector assembly 18 will be referred to hereinafter as a lamp apparatus 20. Lamp apparatus 20 is plugged into a socket assembly 40 constructed according to the present invention.

Lamp apparatus 20 is now described in greater detail with reference to FIG. 3. Reflector assembly 18 is made of a 7251 glass and is manufactured by Corning Glass Works MPWX-1-3, Corning, N.Y. Reflector assembly 18 contains a concave metallic reflector laminated on its interior surface (not shown). Reflector assembly 18 further comprises a convex exterior surface 22 having an upper-half portion 24 and a lower-half portion 26. Projecting from the rear of reflector assembly 18, is a collar 28 integrally formed with the main body of reflector assembly 18. Collar 28 contains a rear aperture 29. Extending through aperture 29 are pin conductors 30 and 32. Pin conductors 30 and 32 are fixed in position by a ceramic or glassy cement compound such as Zirconiumoxide manufactured by Cotronics.

Pin conductors 30 and 32 are each connected to an inlead of D.C. lamp 16. The inleads (not shown) of lamp 16 are essentially wires made of nickle metal. The inleads provide the physical input to lamp 16 for electrical current during the starting and operation of lamp 16. As is well known in HID lamp construction, the inleads are physically connected to foil seals which are, in turn, connected to the electrodes of the lamp. In FIG. 3., pin conductor 30 is in electrical contact with the anode of D.C. lamp 16; and pin conductor 32 is in electrical contact with the cathode of D.C. lamp 16. Details of lamp 16 are not shown because this information is well known to persons skilled in the art relevant to the present invention.

Figure 3:
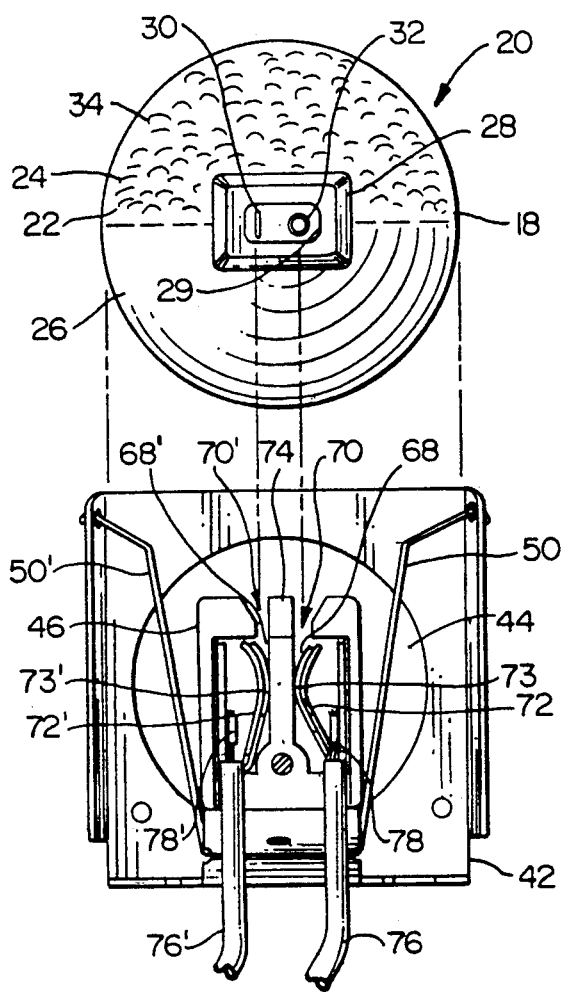
FIG. 3 is a rear elevation view of the socket assembly of FIG. 2 and a D.C. lamp apparatus of the present invention.

As shown in FIG. 3, lamp apparatus 20 further comprises an indicia 34, which may consist of a monochromatic pattern, covering substantially all of upper-half portion 24 of convex exterior surface 22. The purpose of indicia 34 is to indicate the correct orientation of lamp apparatus 20 relative to socket assembly 40. The function of indicia 34 will be described in greater detail below.

Figure 2:
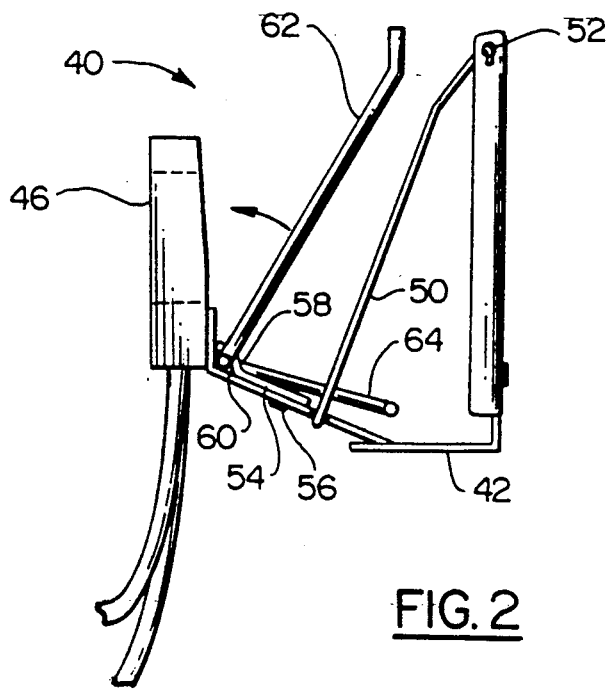
FIG. 2 is a side elevation view of a socket assembly of the present invention.

Referring now to FIG. 2 of the drawings, there is shown a side elevation view of the preferred embodiment of socket assembly 40 according to the claimed invention. Socket assembly 40 comprises a metal support frame 42 containing an optical window 44 (see FIG. 3). Support frame 42 is made of CRS metal. Support frame 42 serves as a support structure for a socket element 46. Socket element 46 is mounted to support frame 42 by a rivet 48 (see FIG. 4). Optical window 44 permits the passage of light emitted from D.C. lamp 16 to an optical system employed in the intended application, such as a projector or instrument (see FIG. 1). Socket element 46 is made of a ceramic material such as Steatite. Socket element 46 is positioned configured and dimensioned to receive pin conductors 30 and 32 of lamp apparatus 20. Socket element 46 will be described in greater detail herein below with reference to FIGS. 3, 5, and 6.

As shown in FIG. 2, socket assembly 40 further comprises support wires 50, 50' for supporting lamp apparatus 20 in its operational position relative to socket element 46. Support wires 50, 50' are mounted to support frame 42 by hooking their respective ends through holes 52, contained in support frame 42 (see FIGS. 2 and 4). Support wires 50, 50' are made of a resilient metal such as "music wire". As shown in FIG. 3, support wires 50, 50' are situated, relative to frame 42, so that reflector assembly 18 of lamp apparatus 20 can be resiliently embraced by support wires 50, 50'.

Figure 4:
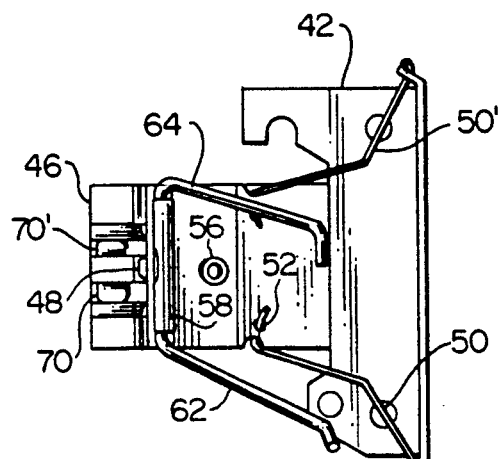
FIG. 4 is a top plan view of the socket assembly of FIG. 2.

With further reference to FIGS. 2 and 4, a metal bracket 54 is mounted to support frame 42 with a rivet 56. Bracket 54 has a bend 58 running across its transverse dimension, at one end thereof (see FIGS. 2 and 4). Bend 58 and an interior surface of support frame 42 together define a lever bearing 60. A lever arm 62 is pivotally coupled to support frame 42 by lever bearing 60. Extending from lever arm 62, is a wedge member 64 which cooperates with lever arm 62 and bearing 60 for levering or unseating lamp apparatus 20 from its supported position within socket assembly 40. Lever arm 62 and wedge member 64 may be realized from a single piece of wire having sufficient strength to accomplish the above-described function.

Support frame 42, in combination with support wires 50, 50', bracket 54, lever arm 62 and wedge member 64, is a conventional assembly available commercially from GTE Sylvania Corporation, Portsmouth Avenue, Exiter, NH 03833. The commercially available combination also includes a conventional socket element.

Socket element 46, constructed in accordance with the present invention, will now be described in detail with reference to FIGS. 3, 5, and 6. Referring to FIG. 6, there is shown a rear elevation view of socket element 46. Socket element 46 has a non-conductive backplate 66 mounted thereto by a rivet 67. Referring now to FIG. 3, there is shown detail of socket element 46 in a rear elevation view with backplate 66 removed. Socket element 46 contains a pair of receptacles 68, 68' configured generally in the form of slots. Receptacles 68, 68' have predetermined widths defined by the opposing interior side walls of the slots at entrance points 70, 70' respectively.

Figure 5:
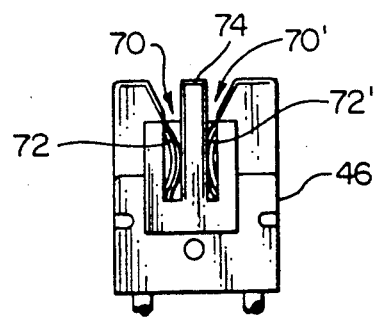
FIG. 5 is a front elevation view of a socket element of the present invention, shown separate from the socket assembly.
Figure 6:
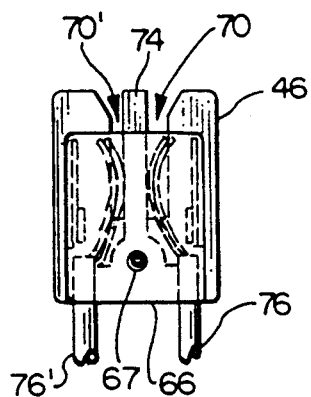
FIG. 6 is a rear elevation view of the socket element of FIG. 5.

The objects of the present invention are achieved in the preferred embodiment by first dimensioning slots 68, 68' such that slot 68' has a width (as defined above) that is smaller than the width of slot 68, as shown in FIGS. 3, 5 and 6. Second, pin conductors 30, 32 are each produced with a transverse configuration distinct from the other. As shown in FIG. 3, anode pin conductor 30 has a transverse configuration substantially in the form of a very narrow rectangle; and cathode pin conductor 32 has a transverse configuration substantially in the form of a circle.

Third, the diameter of the circular configuration of pin conductor 32 is made larger than the width of slot receptacle 68', and made smaller than the width of slot receptacle 68, as shown in FIG. 3. Fourth, the width of the rectangular configuration of pin conductor 30 is made smaller than the width of slot receptacle 68', as shown in FIG. 3.

From the above description, it is apparent that slot receptacle 68' is configured and dimensioned to mate with pin conductor 30 and to prevent such mating with pin conductor 32. In addition, it is apparent that slot receptacle 68 is configured and dimensioned to mate with pin conductor 32.

With further reference to FIG. 3, there is shown a pair of metal contact clips 72 and 72' contained in receptacle 68 and 68' respectively. Contact clips 72, 72' constitute the electrical component of socket element 46, and are used for conducting electricity from an external power supply to D.C. lamp 16. Contact clips 72 and 72' include contact members 73 and 73' respectively. Contact members 73, 73' are made of a resilient metal and are configured and situated within receptacles 68, 68' to urge against a median wall 74. Thus, clips 72, 72' function, in combination with median wall 74, to closely secure or embrace pin conductors 32 and 30 respectively, as lamp apparatus 20 is inserted in socket assembly 40. The close securement of pin conductors 32, 30 within contact clips 72, 72' ensures a good electrical contact between these elements.

Electricity is supplied to socket element 46 by an external power supply (now shown) through a pair of cables 76, 76'. Cable 76 is connected to contact clip 72 at a terminal point 78. Cable 76' is connected to contact clip 72' at a terminal point 78'. Cable 76 supplies a positive potential to contact clip 72, and cable 76' either supplies a negative potential or ground to contact clip 72'.

From the above detailed description, it is apparent that the preferred embodiment of the present invention attains the objective of ensuring that lamp apparatus 20 is inserted into socket assembly 40 in matching polarity. Polarity is matched with respect to lamp apparatus 20 and socket assembly 40 when cathode pin conductor 32 is in electrical contact with a negative potential from receptacle 68 and anode pin conductor 30 is in electrical contact with a positive potential or ground from receptacle 68'.

As shown in FIG. 3, indicia 34 appears on exterior surface 22 of reflector assembly 18. Lamp apparatus 20 is oriented such that indicia 34 faces in a direction away from socket assembly 40 and in clear view of an operator.

The function of indicia 34 is to guide an operator, during a replacement operation, to correctly orient lamp apparatus 20 so that pin conductors 32 and 30 are aligned with receptacles 68 and 68' respectively, in matching polarity. Indicia 34 may indicate a warning that lamp apparatus 20 is in a reverse (or unmatched) polarity position. In this case, indicia 34 may, for example, be simply a solid color red or some other red pattern. Alternatively, indicia 34 may indicate that lamp apparatus 20 is in a matching polarity position, as shown in FIG. 3. In this case, indicia 34 may, for example, be a solid color green or some other green pattern.

In the operation of the preferred embodiment of the present invention, an operator confronted with a failed lamp will first need to remove the lamp assembly. This is accomplished by grasping lever arm 62 and pivoting same in the direction of the arrow shown in FIG. 2. As a result, wedge member 64 will urge against the lamp apparatus and cause it to be substantially released from support wires 50, 50' and socket element 46. The failed lamp assembly can then be easily removed from socket assembly 40.

Next, a replacement lamp assembly 20, embodying the teachings of the present invention, is to be inserted into socket assembly 40. To accomplish this, reflector assembly 18 at one end and pin conductors 32, 20 at the other end of lamp assembly 20 are aligned with support wires 50, 50' and receptacles 68, 68' of socket assembly 40 respectively, as shown in FIG. 3. Then, lamp assembly 20 is manually inserted into socket assembly 40, whereby reflector assembly 18 and pin conductors 32, 30 are closely secured by support wires 50, 50' and slot receptacles 68, 68' respectively. Of course, during the insertion of lamp assembly 20, lever arm 62 should be in the position shown in FIGS. 2 and 4.

If lamp assembly 20 is aligned, relative to socket assembly 40, with its pin conductors 30, 32 in a reverse position from that shown in FIG. 3, conductor 32 will not be able to enter receptacle 68' due to its diameter dimension being greater than the width dimension of receptacle 68'. Accordingly, lamp apparatus 20, is prevented from being inserted into socket assembly 40 in reverse polarity.

If lamp apparatus 20, according to the present invention, includes indicia 34, then the operator will be provided with visual information to assist him or her in correctly orienting lamp apparatus 20, before attempting to insert lamp apparatus 20 into socket assembly 40.

Figure 7:
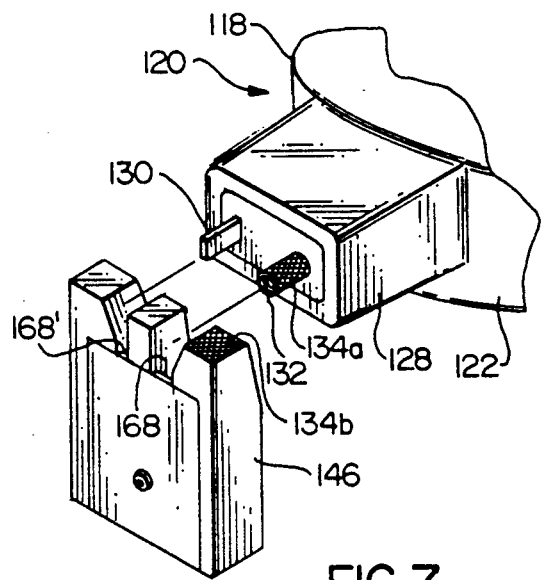
FIG. 7 is an enlarged top and side perspective view of an alternative embodiment of the socket element of the present invention, and an enlarged fragmentary perspective view of an alternative embodiment of a lamp apparatus of the present invention.

Referring now to FIG. 7, it is shown how an indicia means can be alternatively implemented. The reference numerals in FIG. 7 correspond to the reference numerals of FIGS. 1-6, except that they are increased by a value of 100.

A lamp apparatus 120 is provided, having a reflector assembly 118, a convex exterior surface 122, a collar 128, a anode pin conductor 130, and an cathode pin conductor 132. Further, a socket element 146 is provided, having slot receptacles 168, 168'.

A first indicia 134a appears on anode pin conductor 132, and a second indicia 134b appears on socket element 146, as shown in FIG. 7.

During the replacement operation, indicia 134a is aligned with indicia 134b so that lamp apparatus 120 is in matching polarity with socket element 146. That is, pin conductors 132, 130 are aligned with receptacles 168, 168' respectively.

While the invention has been described in the specification and illustrated in the drawings with reference to a preferred embodiment, it will be understood by those skilled in the art that various changes may be made and equivalents may be substituted for elements of the invention without departing from the scope of the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A combination socket and lamp assembly that includes a lamp having a first rectangular shaped blade conductor and a second circular shaped cylindrical conductor, the width of the blade conductor being different from the diameter of the cylindrical conductor, a socket means having a top wall and a front wall, a pair of parallel slotted receptacles formed in said front wall that open upwardly through the top wall, a first receptacle being configured and dimensioned to mate with said first blade conductor and a second receptacle being configured and dimensioned to mate with said second cylindrical conductor so that the lamp connectors can be slidably inserted downwardly into the slots, and electrical contact means contained within the receptacles for transmitting electrical current through the connectors to the lamp.

2. The assembly of claim 1 wherein each receptacle has a funnel-shaped opening passing downwardly through the top wall of the socket means that terminates in a restricted entrance to said receptacle, one entrance being larger than the width of the blade conductor and the other being larger than the cylindrical connector.

3. The assembly of claim 2 that further includes a frame means for supporting the socket means in an upright position and lever means mounted in the frame means for lifting a lamp mated to the socket upwardly whereby the conductors pass out of the receptacles through the top wall of the housing.

4. The assembly of claim 3 that further includes first indicia means on the top wall of the socket means and second indicia means on one of said conductors to indicate the correct orientation of the lamp as it is passed downwardly into the socket means.

* * * * *